(12) United States Patent
Taylor et al.

(10) Patent No.: US 8,754,063 B2
(45) Date of Patent: Jun. 17, 2014

(54) USE OF OLIGOURONATES FOR TREATING MUCUS HYPERVISCOSITY

(75) Inventors: Catherine Taylor, Trondheim (NO);
Kurt Ingar Draget, Trondheim (NO);
Olav Asmund Smidsrod, Trondheim (NO)

(73) Assignee: NTNU Technology Transfers AS, Trondheim (NO)

( * ) Notice: Subject to any disclaimer, the term of this patent is extended or adjusted under 35 U.S.C. 154(b) by 1165 days.

(21) Appl. No.: 12/089,529

(22) PCT Filed: Oct. 6, 2006

(86) PCT No.: PCT/GB2006/003720
§ 371 (c)(1),
(2), (4) Date: Sep. 15, 2008

(87) PCT Pub. No.: WO2007/039754
PCT Pub. Date: Apr. 12, 2007

(65) Prior Publication Data
US 2009/0010914 A1 Jan. 8, 2009

(30) Foreign Application Priority Data
Oct. 6, 2005 (GB) .................................. 0520375.7

(51) Int. Cl.
*A01N 43/04* (2006.01)
*A61K 31/715* (2006.01)

(52) U.S. Cl.
USPC .............................................. 514/54; 514/61

(58) Field of Classification Search
None
See application file for complete search history.

(56) References Cited

U.S. PATENT DOCUMENTS

| | | | |
|---|---|---|---|
| 4,225,592 A | | 9/1980 | Lakatos et al. |
| 5,166,137 A | * | 11/1992 | Otterlei et al. ................. 514/23 |
| 5,459,054 A | | 10/1995 | Skjak-Braek et al. |
| 5,460,957 A | | 10/1995 | Hiura et al. |
| 5,683,991 A | | 11/1997 | Guggenbichler et al. |
| 5,759,572 A | | 6/1998 | Sugimoto et al. |
| 5,795,587 A | | 8/1998 | Gao et al. |
| 5,952,308 A | * | 9/1999 | Nakanishi et al. .............. 514/25 |
| 6,121,441 A | | 9/2000 | Simensen et al. |
| 6,339,075 B1 | | 1/2002 | King et al. |
| 6,407,226 B1 | | 6/2002 | Simensen et al. |
| 6,440,413 B1 | | 8/2002 | Hooreman |
| 6,747,015 B2 | | 6/2004 | Byon et al. |
| 2002/0137723 A1 | * | 9/2002 | Byon et al. ....................... 514/54 |
| 2003/0013678 A1 | | 1/2003 | Lang et al. |
| 2003/0022863 A1 | | 1/2003 | Stahl et al. |
| 2003/0059474 A1 | | 3/2003 | Scott et al. |
| 2003/0224070 A1 | | 12/2003 | Sweazy et al. |
| 2004/0073964 A1 | | 4/2004 | Ellington et al. |
| 2004/0224922 A1 | | 11/2004 | King |
| 2005/0158392 A1 | | 7/2005 | Kim et al. |
| 2006/0083780 A1 | | 4/2006 | Heyes et al. |
| 2009/0010914 A1 | | 1/2009 | Taylor et al. |

FOREIGN PATENT DOCUMENTS

| | | |
|---|---|---|
| CA | 2 428473 A1 | 5/2002 |
| DE | 268865 A1 | 6/1989 |
| DE | 19520743 A1 | 12/1996 |
| EP | 324720 A1 | 7/1989 |
| EP | 506325 A1 | 9/1992 |
| EP | 0888778 A1 | 1/1999 |
| EP | 1234584 | 8/2002 |
| EP | 1714660 A1 | 10/2006 |
| EP | 1745705 A1 | 1/2007 |
| EP | 1837018 A1 | 9/2007 |
| FR | 7576 M | 1/1970 |
| GB | 1042379 A | 9/1966 |
| GB | 2 430 881 A1 | 4/2007 |
| JP | 61-076413 | 4/1986 |
| JP | 01-197431 | 8/1989 |
| JP | 2000-034302 | 2/2000 |
| JP | 2002-338493 A | 11/2002 |
| JP | 2005-145885 | 6/2005 |
| JP | 2006-028041 | 2/2006 |
| WO | WO 88/09794 A1 | 12/1988 |
| WO | WO 91/07951 A1 | 6/1991 |
| WO | WO 91/11205 A1 | 8/1991 |
| WO | WO 95/18145 A1 | 7/1995 |
| WO | WO 98/13024 A2 | 4/1998 |
| WO | WO 01/15672 A2 | 3/2001 |
| WO | WO 01/17506 A1 | 3/2001 |
| WO | WO 01/66084 A2 | 9/2001 |
| WO | WO 01/72278 A2 | 10/2001 |
| WO | WO 2007/002224 A2 | 1/2004 |
| WO | WO 2005/089722 A1 | 9/2005 |
| WO | WO 2007/002224 A2 | 1/2007 |
| WO | WO 2007/039754 A1 | 4/2007 |
| WO | WO 2007/039760 A2 | 4/2007 |
| WO | WO 2007/046719 A2 | 4/2007 |

(Continued)

OTHER PUBLICATIONS

Fiel et al. (CHEST, vol. 108, pp. 153-156; 1995).*

(Continued)

*Primary Examiner* — Jeffrey S. Lundgren
*Assistant Examiner* — Michael Schmitt
(74) *Attorney, Agent, or Firm* — Knobbe, Martens, Olson & Bear, LLP (57) ABSTRACT

A method of treatment of a human or non-human subject to combat mucosal hyperviscosity in the respiratory tract, which method includes application to a mucosal surface in the tract in the subject of an effective amount of a physiologically tolerable oligouronate. Related compositions containing physiologically tolerable oligouronates are also described.

12 Claims, 6 Drawing Sheets

(56) References Cited

FOREIGN PATENT DOCUMENTS

| WO | WO 2008/125828 A2 | 10/2008 |
|---|---|---|
| WO | WO 2008/137114 A1 | 11/2008 |
| WO | WO 2009/142892 A2 | 11/2009 |

OTHER PUBLICATIONS

Grasdalen, H. et al. 1979 "A.P.M.R. study of the composition and sequence of urinate residues in alginates" *Carbohydrate Research* 68: 23-31.
Aikiyama, Hisayoshi et al. (1991) "Effect of Depolymerized Alginates on the Growth of Bifidobacteria" *Biosci. Biotech. Biochem* 56: 355-356.
Chono, S. et al. 2008 "An efficient and low immunostimulatory nanoparticle formulation for systemic siRNA delivery to the tumor" *Journal of Controlled Release* 131: 64-69.
Dalby, B. et al. 2004 "Advanced transfection with Lipofectamine 2000 reagent: primary neurons, siRNA, and high-throughput applications" *Methods* 33: 95-103.
Eiselt, Petra et al. (2000) "Porous carriers for biomedical applications based on alginate hydrogels" *Biomaterials* 21: 1921-1927.
Jiang, G. et al. 2007 "DNA/PEI/Alginate polyplex as an efficient in vivo gene delivery system" *Biotechnology and Bioprocessing Engineering* 12: 684-689.
Klöck, G. et al. 1997 "Biocompatibility of mannuronic acid-rich alginates" *Biomaterials* 18: 707-713.
Kong, H. J. et al. 2008 "Design of Biodegradable Hydrogel for the Local and Sustained Delivery of Angiogenic Plasmid DNA" *Pharaceutical Research* 25: 1230-1238.
Krebs, M. D. et al. 2009 "Localized and Sustained Delivery of Silencing RNA from Macroscope Biopolymer Hydrogels" *Journal of the American Chemical Society* 131: 9204-9206.
Pandey, Rajesh & Khuller, G.K. (2005) "Chapter 27: Alginate as a Drug Delivery Carrier" *Handbook of Carbohydrate Engineering* pp. 799-815.
Rakkhithawatthana, V. et al. 2010 "Investigation of gene transferring efficacy through nano-polyplex consisting of methylated N-(4-pyridinylmethyl) chitosan chloride and poly(ethylenimine) in human cell lines" *Carbohydrate Polymers* 80: 276-284.
Sioud, M. et al. 2003 "Cationic liposome-mediated delivery of siRNAS in adult mice" *Biochemical and Biophysical Research Communications* 312: 1220-1225.
Tadashi, Yoshimatsu et al. (2002) "Effects on Intestinal Flora of a Beverage Containing Non-fermentable Depolymerized Sodium Alginate and Water-soluable Fermentable Corn Bran Fiber" *The Journal of Nutrition and Dietetics* 60: 137-143.
Terada, A. et al. (1995) "Effect of Dietary Alginate on the Faecal Microbiota and Faecal Metabolic Activity in Humans" *Microbial Ecology in Health and Disease* 8: 259-266.
Yun, Y. H. et al. 2004 "Hyaluronan microspheres for sustained gene delivery and site-specific targeting" *Biomaterials* 25: 147-157.
Westedt, U. et al. 2007 "Poly(vinylalcohol)-graft-poly(lactide-co-glycolide) nanoparticles for local delivery of paclitaxel for restenosis treatment" *Journal of Controlled Release* 119: 41-51.
FMC Biopolymer 2003 "A world of possibilities lies just below the surface: Alginates" Brochure (in 20 pages).
Ikeda, A. and Ono T.H. 2000 "Preparation of low-molecular weight alginic acid by acid hydrolysis" *Carbohydrate Polymers* 42: 421-425.
Banning D. et al. 1997 "Oscillatory and thermorheological characterization of alginate/mucin mixes" Pharmacy and Pharmacology (British Pharmaceutical Conference 1997 Science proceedings 134th meeting, Scarborough, Sep. 15-18, 1997, Abstract 65.
Murata, K. et al. 1992 "Continuous depolymerization of alginates by a non-support bioreactor system containing flocculated bacterial cells" *Journal of Fermentation and Bioengineering* 73:172-174.
Tang, J.X. et al. 2005 "Anionic poly(amino acid)s dissolve F-actin and DNA bundles, enhance DNase activity, and reduce the viscosity of cystic fibrosis sputum" *Am J Physiol Lung Cell Mol Physiol* 289:L599-L605.
Iwamoto, M. et al. 2005 "Structure—activity relationship of alginate oligosaccharides in the induction of cytokine production from RAW264.7 cells" *FEBS Letters* 579: 4423-4429.
Witschi, C. et al. 1999 "In vitro evaluation of microparticles and polymer gels for use as nasal platforms for protein delivery" *Pharmaceutical Research* 16: 382-390.
Shidrawi, R.G.et al. 2002;"Emergency colonoscopy for distal intestinal obstruction syndrome in cystic fibrosis patients", *Gut*; 51: 285-286.
Shraishi, S. et al. J., 1991: "Improvement of Absorption Rate of Indomethacin and Reduction of Stomach Irritation by Alginate Dispersions" *J Pharm. Pharmacol* 43: 615-620.
Hanninen, A. and Harrison, L.C. 2004 "Mucosal Tolerance to Prevent Type 1 Diabetes: Can the Outcome Be Improved in Humans?" *Rev Diabet Stud* 1: 113-121.
Merck Manual, "Disorders," www.merckmanuals.com/professional/index.html, accessed Aug. 6, 2012.
Merck Manual, "Diseases," www.merckmanuals.com/professional/index.html, accessed Aug. 6, 2012.
Merck Manual, "Diabetes," www.merckmanuals.com/professional/index.html, accessed Aug. 6, 2012.

* cited by examiner

USE OF OLIGOURONATES FOR TREATING MUCUS HYPERVISCOSITY

This application is U.S. National Phase of International Application PCT/GB2006/003720, filed Oct. 6, 2006 designating the U.S., and published in English as WO 2007/039754 on Apr. 12, 2007, which claims priority to Great Britain Patent Application No. 0520375.7 filed Oct. 6, 2005.

This invention relates to a method of treatment of human or non-human animals, in particular mammals, with oligouronates to combat elevated mucosal viscosity, e.g. to enhance mucus clearance, especially from the respiratory tract such as in the case of COPD's (chronic obstructive pulmonary diseases), in particular the sinuses and the lungs, in particular in the treatment of cystic fibrosis (CF), chronic obstructive pulmonary disease and sinusitis.

Cystic fibrosis is the most common lethal genetic disease in European populations. The disease is caused by a mutation in the gene that codes for the cystic fibrosis transmembrane regulator (CFTR), a chloride channel that is present in secretary and other cells in the body. The disease is characterized by the presence of thick, intractable mucus secretions in the body that can lead to lung disease, digestive problems and infertility. The normal pattern of mucociliary clearance in the lungs fails to clear the unduly viscous mucus which becomes colonized by microorganisms, which in turn increases mucus viscosity and may lead to chronic lung inflammation and obstruction. Lung disease is thus the biggest health problem for the majority of CF patients and is the major cause of death.

Mucus is a normal secretion of the entire respiratory tract, including the lungs. Its primary function is as part of the mucociliary clearance system that keeps the lungs clean and protects against infection. The mucociliary clearance system has three main components: mucus; cilia; and the airway surface liquid. The epithelial surface thus comprises mucus secreting goblet cells and ciliated epithelial cells with an overlying layer of airway surface liquid and above that a layer of mucus, into which the tips of the cilia protrude. The mucus is a sticky gel material composed primarily of water (about 95% wt.) and mucins, gel forming molecules responsible for the physical properties of the mucus. The cilia are small hair-like projections from the surface of the epithelial cells, which beat rhythmically in the watery, non-viscous airway surface liquid with their tips immersed in the mucus layer. The mucus layer forms a sticky blanket on the lung surface that traps bacteria, viruses, inhaled particles, environmental pollutants and cell debris. The beating of the cilia serves to propel this mucus blanket and anything trapped in it towards the mouth and out of the lungs. Under normal conditions, the mucociliary clearance system functions effectively and the lungs are kept clean and free of infection. If the system is overwhelmed, there is a second line of defence-cough. Thus when increased levels of mucus are secreted in response to irritation or inflammation, e.g. due to inhaled particles or infection, the mucus is projected out of the lungs by the cough reflex.

In CF patients the mucus in the lung is thicker and more viscous than normal, and this thicker mucus is not so easily transported by the cilia. As a result the mucociliary clearance system is compromised and the lungs are more vulnerable to infection. In addition, the lungs of CF patients appear to be in a hyper-inflammatory state with a continual low level of inflammation and a heightened response to agents that normally cause inflammation. This is problematic as part of the response to inflammation is increased production of mucus. The increased mucus builds up if it is too thick to be cleared by the mucociliary clearance system or coughing, lung capacity is reduced and the exchange of oxygen across the mucosa is decreased. This provides an ideal environment for bacterial colonisation, a serious problem for CF patients as it also causes inflammation and activates the immune response. This leads not only to increased mucus secretion but also an increased presence of immune response cells and agents such as macrophages and lysozymes. As bacteria and macrophages die, their cell contents are released into the mucus and these include viscous molecules such as DNA. Furthermore, some of the bacteria, e.g. *Burkholderia* sp. and *Pseudomonas aeruginosa*, also secrete highly viscous polysaccharides, in the latter case alginates. These molecules further increase the viscosity of the mucus, in the case of the alginates apparently by interaction with the mucin matrix of the mucus but in the case of DNA apparently by increasing the viscosity of the sol phase within the mucin matrix.

Maintaining the mucus in a form capable of being transported by the cilia is thus a key goal of treatment of CF. Agents which simply break down its gel-like structure would result in fluid which was as untransportable as the hyperviscous mucus of the CF patient. It is important therefore that any treatment agent should not break down the gel matrix formed by the glycoprotein mucins.

We have now found that this can be achieved using oligouronates, i.e. multiply charged hydroxyl group carrying oligomers, in particular one containing two to thirty monomer residues.

Elsewhere in the respiratory tract, in particular in the sinuses, especially the paranasal sinuses, overly viscous mucous can present problems. Oligouronates, can also be used to address these problems.

Thus, viewed from one aspect the invention provides a method of treatment of a human or non-human (e.g. mammalian) subject to combat mucosal hyperviscosity in the respiratory tract, e.g. to treat chronic obstructive pulmonary disease, sinusitis or cystic fibrosis patients, which method comprises application to a mucosal surface in said tract in said subject of an effective amount of a physiologically tolerable oligouronate polyol.

Viewed from a further aspect the invention provides the use of a physiologically tolerable oligouronate for the manufacture of a medicament for use in the treatment of mucosal hyperviscosity in the respiratory tract.

The application of the oligouronate may be by any means which delivers it to a mucus secreting, or mucus carrying surface in the patient's respiratory tract, e.g. the paranasal sinuses or more preferably the lungs. Introduction will typically be by inhalation, e.g. of liquid droplets (for example an aerosol) or a powder.

The counterions for the oligouronate may be any of the physiologically tolerable ions commonly used for charged drug substances, e.g. sodium, potassium, ammonium, chloride, mesylate, meglumine, etc. Ions which promote alginate gelation, e.g. group 2 metals, however will preferably not be used.

While the oligouronate may be a synthetic material, it is preferably a derivative, having a weight average molecular weight of less than 100000 Da, of a naturally occurring polysaccharide. It is preferably a 3- to 28-mer, in particular a 4- to 25-mer, especially a 6- to 22-mer, in particular an 8- to 15-mer, especially a 10-mer, e.g. having a molecular weight in the range 350 to 6000 Da especially 750 to 4500 Da. It may be a single compound or it may be a mixture of oligouronate compounds, e.g. of a range of degrees of polymerization. Moreover, the monomeric residues in the oligouronate, e.g. the monosaccharide groups, may be the same or different and not all need carry electrically charged groups although it is preferred that the majority (e.g. at least 60%, preferably at least 80% more preferably at least 90%) do. It is preferred that a substantial majority, e.g. at least 80%, more preferably at least 90% of the charged groups have the same polarity. In the oligouronate, the ratio of hydroxyl groups to charged groups is preferably at least 2:1, more especially at least 3:1.

Oligouronates are readily accessible from natural sources since many natural polysaccharides contain charged uronate residues, e.g. residues such as guluronic and galacturonic acid residues.

Polysaccharide to oligosaccharide cleavage to produce oligosuronate useable according to the present invention may be performed using conventional polysaccharide lysis techniques such as enzymatic digestion and acid hydrolysis. Oligouronates may then be separated from the polysaccharide breakdown products chromatographically using an ion exchange resin or by fractionated precipitation or solubilization.

The oligouronates may also be chemically modified, including but not limited to modification to add charged groups (such as carboxylated or carboxymethylated glycans), and oligouronates modified to alter flexibility (e.g. by periodate oxidation)

Suitable polysaccharides are discussed for example in "Handbook of Hydrocolloids", Ed. Phillips and Williams, CRC, Boca Raton, Fla., USA, 2000. The use of alginates however is especially preferred as these naturally occur as block copolymers of manuronic (M) and guluronic (G) acids and G-block oligomers can readily be produced from alginate source materials. Indeed, in general the oligouronate is preferably an oligoguluronic acid, or less preferably an oligogalacturonic acid.

Where alginates are used as the starting material for preparation of the oligouronate, the guluronic acid content may if desired be increased by epimerization with mannouronan C-5 epimerases from *A. vinelandii*.

Oligoguluronic acids suitable for use according to the invention may conveniently be produced by acid hydrolysis of alginic acid from *Laminaria hyperborea*, dissolution at neutral pH, addition of mineral acid to reduce the pH to 3.4 to precipitate the oligoguluronic acid, washing with weak acid, resuspension at neutral pH and freeze drying.

Viewed from a further aspect the invention also provides a pharmaceutical composition, especially an inhalable composition, e.g. a solution, suspension, dispersion or powder, comprising a physiologically tolerable oligouronate together with a physiologically tolerable carrier or excipient, and preferably also a further physiologically tolerable mucosal viscosity reducing agent, e.g. a nucleic acid cleaving enzyme (e.g. a DNAse such as DNase I), gelsolin, a thiol reducing agent, an acetylcysteine, sodium chloride, an uncharged low molecular weight polysaccharide (e.g. dextran), arginine (or other nitric oxide precursors or synthesis stimulators), or an anionic polyamino acid (e.g. poly ASP or poly GLU). The use of a DNase is especially preferred. The oligouronate may be administered typically in doses of 1 to 10000 mg, especially 10 to 1000 mg for an adult human. The optimum does may readily be determined by routine dosage ranging experiments, optionally following initial investigation of an animal model, e.g. a dog model.

The compositions of the invention may be produced using conventional pharmaceutical carriers and excipients, e.g. solvents (such as water), osmolality modifiers, flavours, pH regulators, etc. They may contain additional active components, for example agents which serve to break down biopolymers not involved in the mucin matrix of the mucus (e.g. DNase, particularly rhDNase), antibacterial agents, and anti-inflammatories. Combination therapy using a such further agent and the oligouronate, administered separately or together is a particularly preferred aspect of the method of the invention. Such further agents may be used in their normal doses or even at lower doses, e.g. 50% of normal dose.

The oligouronates are desirably administered as a spray, preferably an aerosol spray made from an aqueous solution or in the form of powders, e.g. of approximately nanometer to micrometer (e.g. 10 to 50000 nm) mode particle size by volume size.

Viewed from a further aspect the invention provides a spray applicator comprising a reservoir and a droplet generator, said reservoir containing an aqueous solution of a physiologically tolerable oligouronate. Such spray applicators, and indeed the oligouroantes, may be used in the treatment of sinus or nasal blockage or congestion resulting from the common cold or other reasons.

The invention will now be described further with reference to the following non-limiting Examples and the accompanying drawings, in which:

FIGS. 7*a* and 7*b* show the phase angle $\delta$ for treated and untreated sputum samples. FIG. 7*b* showing $\delta$ as a percentage of control.

EXAMPLE 1

The effect of five oligomeric materials on a model mucin-alginate gel were tested:
a) Low molecular weight dextran (6000 Da)
b) Low molecular weight PEG (3350 Da)
c) Low molecular weight DNA
d) Sodium galacturonate oligomers
e) Sodium guluronate oligomers (G blocks)

The sodium guluronate oligomer was prepared as described above and had the following characteristics:

$F_G$ 0.87, $F_M$ 0.13, $F_{GG}$ 0.83, $F_{GM}=F_{MG}$ 0.05, $F_{MM}$ 0.08, $F_{GGM}=F_{MMG}$ 0.04, $F_{MGM}$ 0.02, $F_{GGG}$ 0.79, DP 19.

Materials

Control gel consisted of 18 mg/ml mucin+0.6 mg/ml alginate in 0.05M NaCl

Test gels consisted of 18 mg/ml mucin+0.6 mg/ml alginate+4 mg/ml test material in 0.05 M NaCl Rheological Tests Gelation—immediately after mixing the sample was loaded into the rheometer at 37° C. The temperature was cooled to 10° C. (0.5 degree/min) and then held at 10° C. for 18 hours. The behaviour of the sample and gel development was measured continuously.

Frequency sweep—after gelation the temperature of the sample was raised to 37° C. and the rheological behaviour monitored as a function of frequency.

Stress sweep—at 37° C., the behaviour of the gel was monitored as a function of increasing applied stress.

Gelation

The studies demonstrated that sodium guluronate oligomers (G blocks) are able to displace alginate in mucin-alginate interactions as seen by the decrease in the complex modulus of the gel (G*) over time after the initial gelation. For the five test gels and the control gel this is shown in FIGS. 1a to 1f respectively.

Of the other oligomeric materials tested only sodium galacturonate oligomers had a similar effect, showing a decrease in the moduli values over time. The other materials (DNA, PEG, dextran) caused a delay in gelation but the gel continued to develop over time as shown by the increase in complex modulus.

Figure 1A:
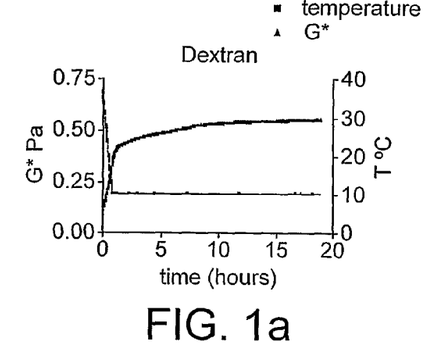
FIGS. 1*a* to 1*f* are plots of complex modulus over time for a mucin-alginate gel and for the same gel dosed with dextran, polyethylene glycol, DNA, sodium galacturonate oligomer and sodium guluronate oligomer respectively.
Figure 1B:
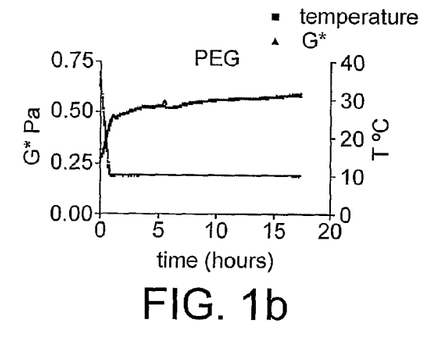
Figure 1C:
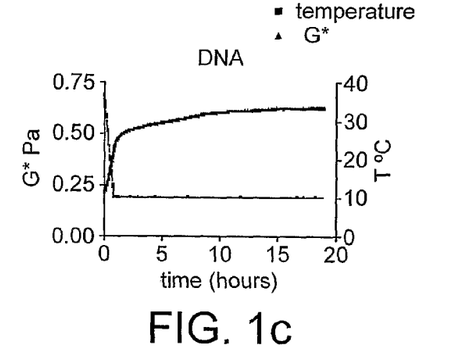
Figure 1D:
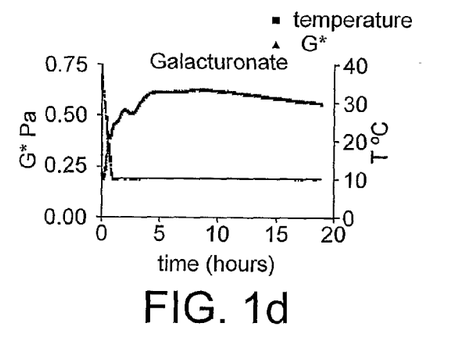
Figure 1E:
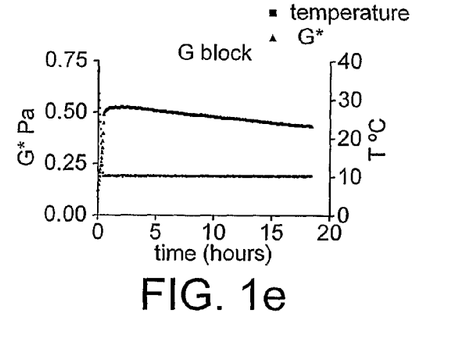
Figure 1F:
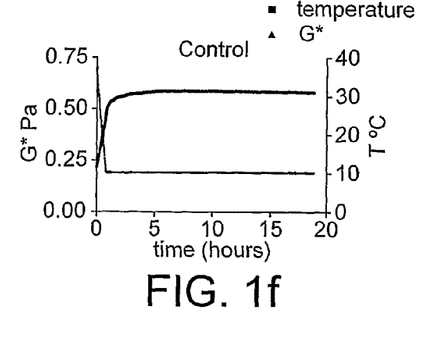
Figure 2:
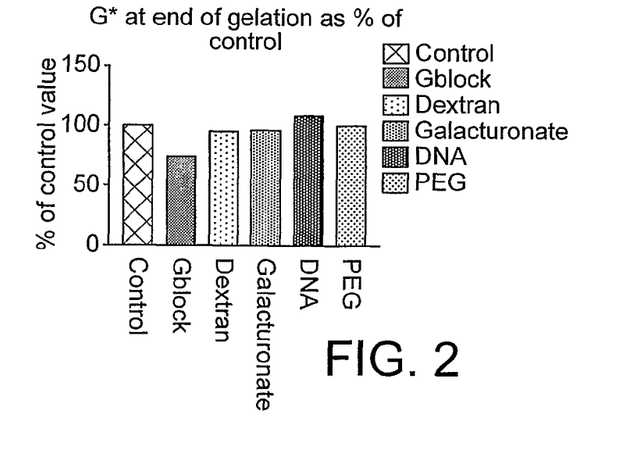
FIGS. 2 and 3 are bar charts showing the complex modulus (G*) and the phase angle of the same gels at the end of gelation as a percentage of the control.
Figure 3:
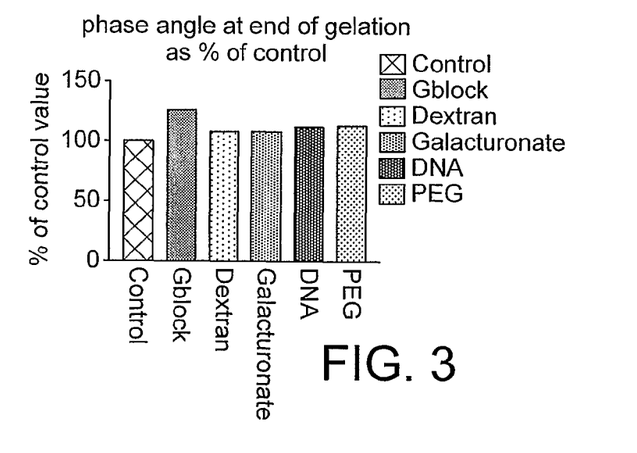

The complex modulus and phase angle of the gels at the end of the gelling period is plotted in FIGS. 2 and 3. The complex modulus is a measure of the total response or strength of the system and the phase angle concerns the balance between liquid like and solid like behaviour with a higher phase angle indicating greater liquid like behaviour. Sodium guluronate oligomers (G blocks) caused the greatest drop in G* and the greatest increase in the phase angle.

Gel Behaviour from the Frequency Sweep

All the gels showed frequency sweep behaviour typical of weak viscoelastic gels.

Flow Stress from the Stress Sweep

Figure 4:
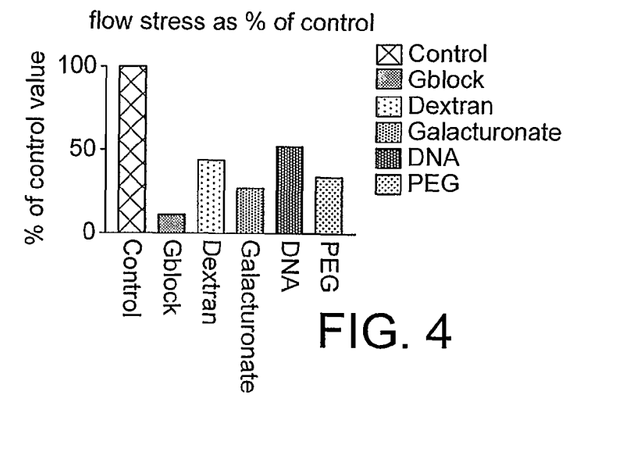
FIG. 4 is a bar chart showing the flow stress of the same gels, again as a percentage of the control.

A stress sweep was used to determine the stress needed to induce flow in the system. This is plotted in FIG. 4 as a % of the stress needed to induce flow in the control gel. This gives an indication of how much the added material has weakened the gel matrix. G blocks (sodium guluronate oligomers) had the most pronounced effect on the flow stress followed by sodium galacturonate oligomers.

EXAMPLE 2

Effect on Sputum

Sputum samples were collected from cystic fibrosis patients with a positive diagnosis for *Pseudomonas aeruginosa* infection. The samples were gently stirred, divided into portions, frozen and stored at −40° C.

Pre-Testing Procedure:

The sputum samples were taken out from the freezer and placed in the fridge (4° C.) one hour before testing, stirred on a magnetic stirrer for about 10 min and divided into 0.5 g portions. Testing media was added to all but one sample, the pure sputum sample. The resulting samples were:

A 0.5 g sputum (pure)

B 0.5 g sputum+65 µl 350 mM NaCl solution (ionic strength of the added guluronate oligomer)

C 0.5 g sputum+75 µl 150 mg/ml Sodium guluronate oligomers Dp19

D 0.5 g sputum+75 µl 150 mg/ml Sodium guluronate oligomers Dp10

The sodium guluronate oligomer Dp 10 (degree of polymerization) had the following characteristics:

$F_G$ 0.79, $F_M$ 0.11, $F_{GG}$ 0.76, $F_{GM}=F_{MG}$ 0.03, $F_{MM}$ 0.07, $F_{MGG}=F_{GGM}$ 0.02, $F_{MGM}$ 0.01, $F_{GGG}$ 0.74, $F_G$(red) 0.10, $F_G$(tot) 0.89, $N_{G>1}$ 37, Dp 10

The mixed samples were then gently stirred for 1 min and subsequently placed into the fridge for 5 min before being transferred to the rheometer for testing.

Rheological Testing:

Rheological measurements of the pure and mixed sputum was carried out on plate/cone (40 mm/1°) using a Rheologica Stress-Tech general purpose rheometer at 10° C. to minimize the effect of proteolytic enzymes.

The rheological characterisation of the pure sputum and sputum mixed with testing media was performed in four different steps:

Oscillating strain control for 2 min with constant strain 0.03 and frequency at 1 Hz.

Oscillating strain control after pre-shear (1 min at 20 s$^{-1}$ shear rate) for 60 min with constant strain at 0.03 and frequency at 1 Hz.

Frequency sweep with range from 0.01-5 Hz at constant strain 0.03.

Stress sweep with range from 0.02-20 Pa at 1 Hz.

Figure 5A:
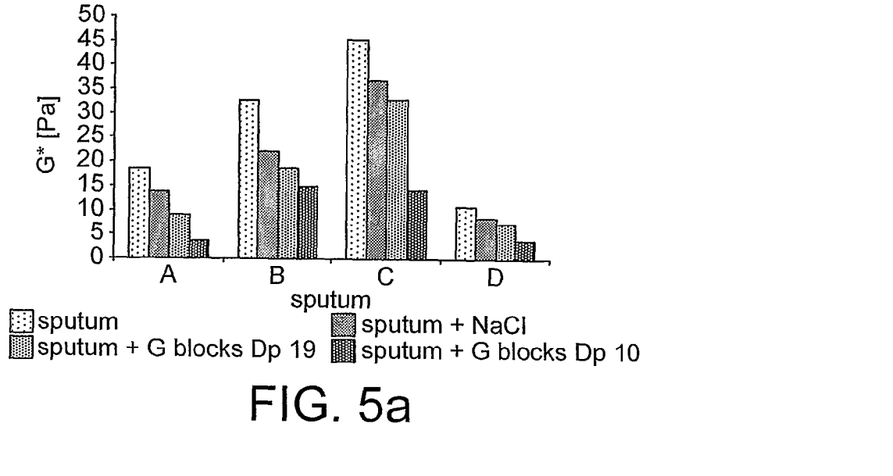
FIGS. 5*a* and 5*b* show the complex modulus G* for treated and untreated sputum samples from CF patients, FIG. 5*b* showing G* as a percentage of control (the untreated sputum)
Figure 5B:
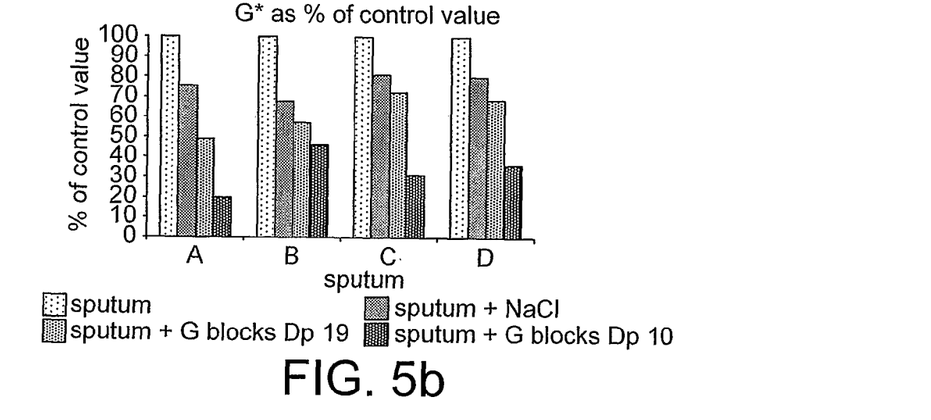
Figure 5C:
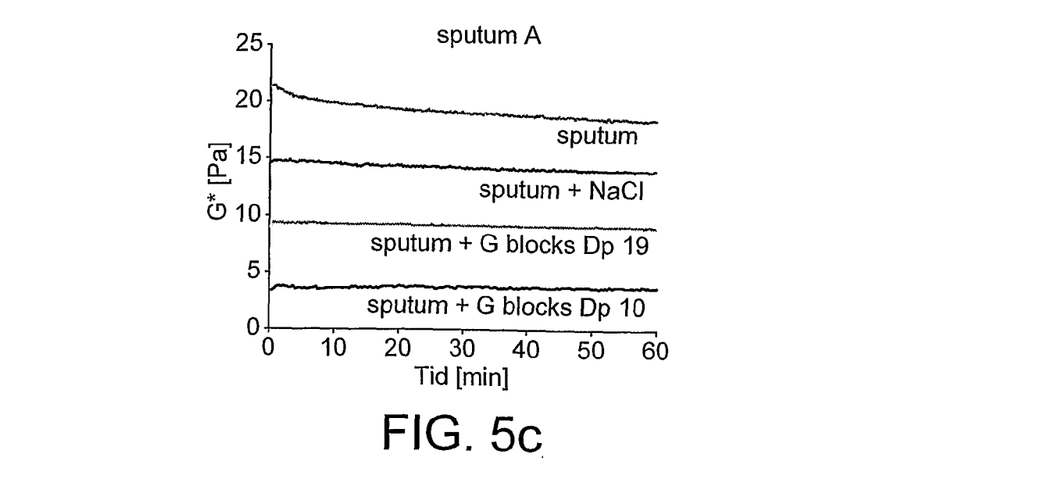
FIGS. 5*c* to 5*f* show plots of G* over time.
Figure 5D:
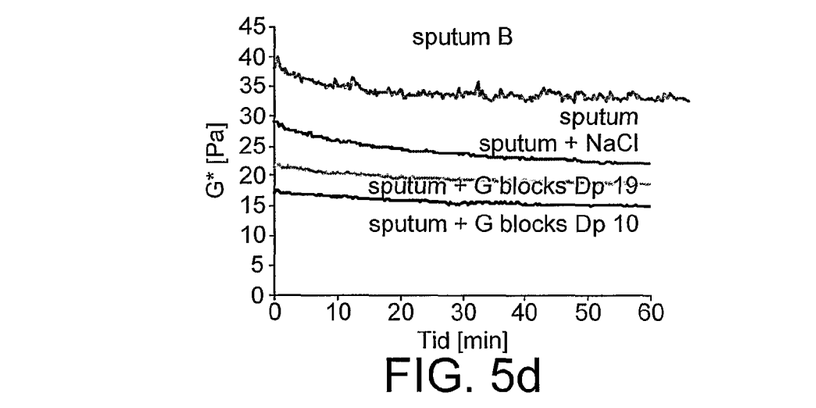
Figure 5E:
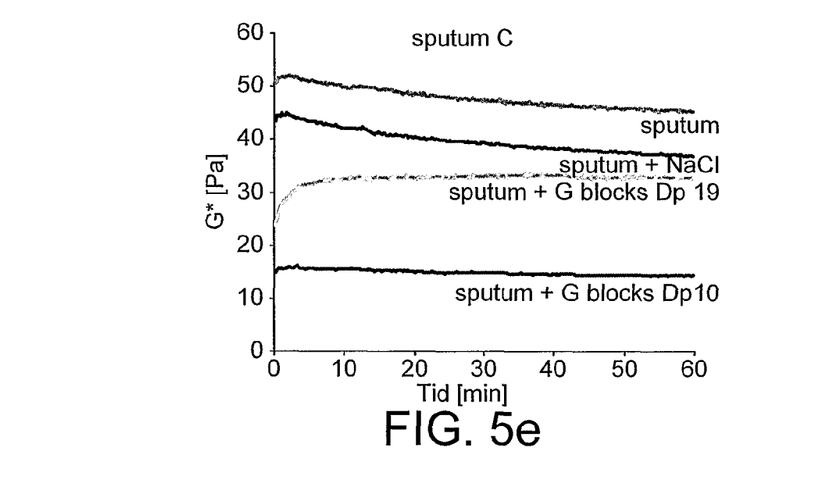
Figure 5F:
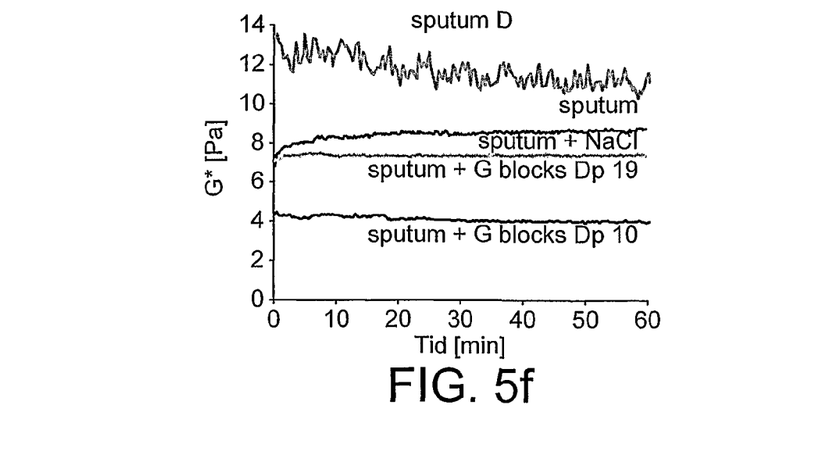

FIG. 5a is bar chart showing the complex modulus (G*) for the sputum samples at the end of testing, after 60 min. FIG. 5b is bar chart showing the same sputum samples as in FIG. 5a, but as percentage of the control (pure sputum).

FIGS. 5c to 5f are plots of complex modulus over time for the sputum samples A to D.

Figure 6A:
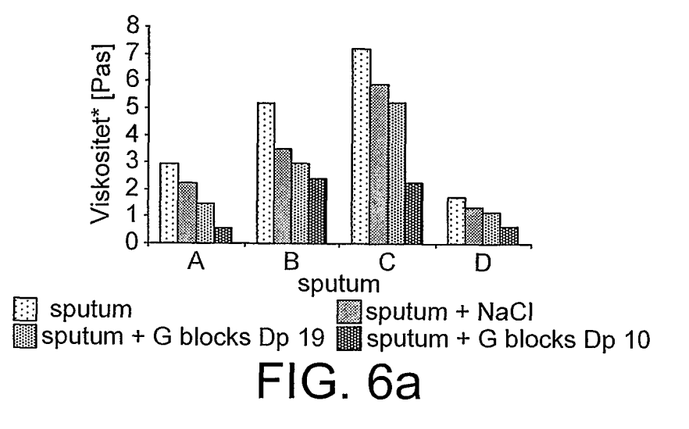
FIGS. 6*a* and 6*b* show the complex viscosity ($\eta$*) for treated and untreated sputum samples, FIG. 6*b* showing $\eta$* as a percentage of control.
Figure 6B:
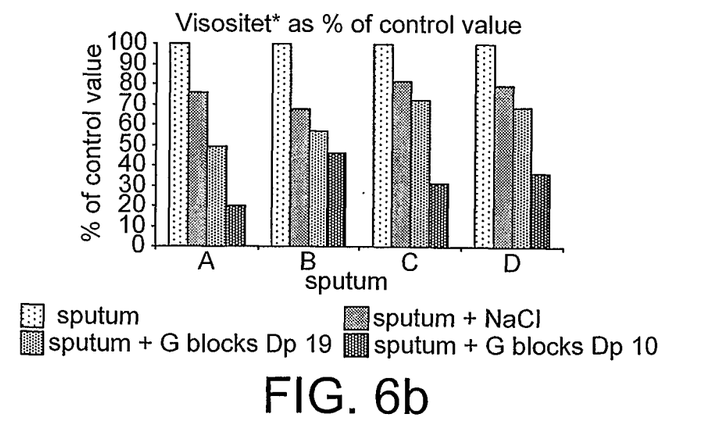

FIG. 6a is bar chart showing the complex viscosity (η*) for the sputum samples at the end of testing, after 60 min. FIG. 6b is bar chart showing the same sputum samples as in FIG. 6a, but as percentage of the control.

Figure 7A:
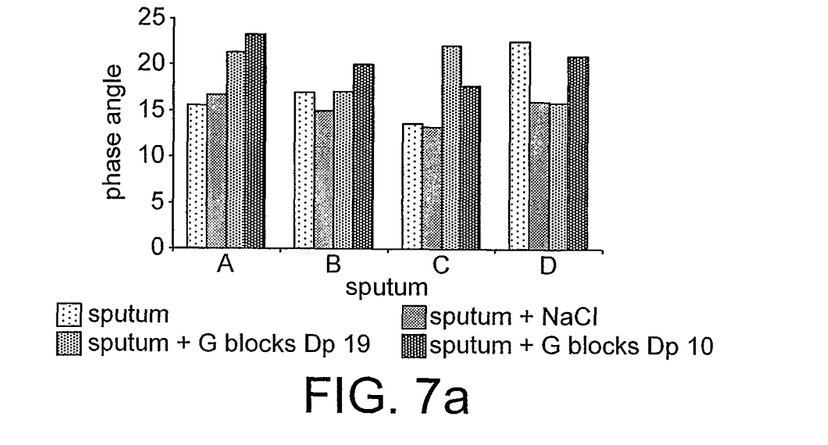

FIG. 7a is bar chart showing the phase angle (δ) for the sputum samples at the end of testing, after 60 min.

Figure 7B:
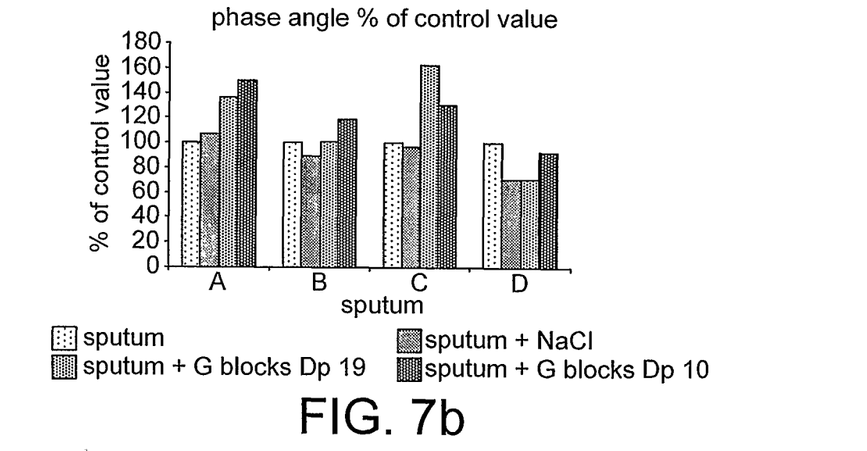

FIG. 7b is bar chart showing the same sputum samples as in FIG. 3a, but as percentage of the control.

Addition of guluronate oligomers obviously reduces the mechanical properties of CF sputum ex vivo. Both the complex dynamic modulus as well as the complex dynamic viscosity is considerably reduced, in some cases by as much as a factor of 5. Dp 10 appears to be more effective than the sample with an average Dp of 19. Results obtained from preparing the sputum samples as described also suggest that the CF sputum obtain equilibrium-like mechanical properties faster in the presence of Dp 10 G-blocks than in the presence of other components (G* and η* independent upon time). The change in the phase angle is, however, not effected to such an extent as G* and η*. This is most important since it clearly shows that the mechanical properties of the mucin network is preserved and hence still able to function as a first line of defence against air-borne pollutants.

EXAMPLE 3

Aerosol

A sterile aerosol spray, administered by the aid of a nebuliser, is made from a liquid containing 3-10% of the sodium salt of a guluronic acid block with a purity of at least 75% guluronate and a degree of polymerisation between 5 and 20, and, if necessary, a surface active compound to stabilise the aerosol droplet size.

The invention claimed is:

1. An inhalable pharmaceutical composition comprising a physiologically tolerable oligouronate together with a physiologically tolerable carrier or excipient, wherein said physiologically tolerable oligouronate is a linear 3- to 28-mer obtainable by polysaccharide lysis from a natural polysaccharide containing charged uronate residues.

2. The composition as claimed in claim 1 containing a further physiologically tolerable mucosal viscosity reducing agent.

3. The composition as claimed in claim 1, wherein said oligouronate comprises guluronic acid as a monomer or wherein said oligouronate is a 4- to 25-mer.

4. The composition as claimed in claim 1 further containing a DNase.

5. A spray applicator comprising a reservoir and a droplet generator, said reservoir containing an aqueous solution of the composition according to claim 1.

6. A method of treatment of a human or non-human subject to combat mucosal hyperviscosity in the respiratory tract comprising applying to a mucosal surface in said tract in said subject an effective amount of the composition according to claim 1.

7. The method as claimed in claim 6 for the treatment of cystic fibrosis.

8. The method as claimed in claim 6 for the treatment of sinusitis.

9. The method as claimed in claim 6 for the treatment of chronic obstructive pulmonary diseases.

10. The method as claimed in claim 6 wherein said oligouronate is administered into the patient's airway.

11. The method as claimed in claim 6 wherein said oligouronate comprises guluronic acid as a monomer.

12. The method as claimed in claim 6 wherein said oligouronate is a 4- to 25-mer.

* * * * *